(12) United States Patent
Ohyama

(10) Patent No.: US 7,479,506 B2
(45) Date of Patent: Jan. 20, 2009

(54) AGENT OR METHOD FOR TREATING SEVERE APHASIA IN CEREBROVASCULAR ACCIDENT CHRONIC STAGE

(76) Inventor: Hideki Ohyama, 5-29-17-3, Nankodai, Izumi-ku, Sendai-shi, Miyagi (JP) 981-8003

( * ) Notice: Subject to any disclaimer, the term of this patent is extended or adjusted under 35 U.S.C. 154(b) by 0 days.

(21) Appl. No.: 10/584,155

(22) PCT Filed: Dec. 24, 2004

(86) PCT No.: PCT/JP2004/019373
§ 371 (c)(1),
(2), (4) Date: Jun. 22, 2006

(87) PCT Pub. No.: WO2005/061454
PCT Pub. Date: Jul. 7, 2005

(65) Prior Publication Data
US 2007/0185190 A1  Aug. 9, 2007

(30) Foreign Application Priority Data
Dec. 24, 2003 (JP) ............................. 2003-427424

(51) Int. Cl.
*A61K 31/4015* (2006.01)
*A61P 25/00* (2006.01)
*A61P 25/28* (2006.01)

(52) U.S. Cl. ..................................... 514/424

(58) Field of Classification Search ........................ None
See application file for complete search history.

(56) References Cited

FOREIGN PATENT DOCUMENTS

RU  2145895 C1  2/2000

OTHER PUBLICATIONS

Dudley, Alden. W. "Stroke." Grolier Multimedia Encyclopedia. Grolier Online http://gme.grolier.com/cgi-bin/article?assetid=0278580-0, pp. 1-3 (accessed Aug. 2, 2007).*
"Ischemic Stroke", The Merck Manual, 17th Edition, 1999, pp. 1421-1422.*
J.-M. Orgogozo: "Piracetam in the Treatment of Acute Stroke" CNS Drugs, ADIS International, vol. 9 No. 1, 1998, pp. 41-49.
Klaus Poeck: "Piracetam Treatment in Post-Stroke Aphasia" CNS Drugs, ADIS International, vol. 9, No. 1, 1998, pp. 51-59.
Stuart Noble et al: "Piracetam: A Review of its Clinical Potential is the Management of Patients With Stroke" CNS Drugs, ADIS International, vol. 9. No. 6,1998, pp. 497-511.
De Reuck J et al: "The Clinical Safety of High-Dose Piracetam—Its Use in the Treatment of Acute Stroke" Pharmacopsychiatry, Georg Thieme Verlag, Stuttgart, DE., vol. 32, No. 1, 1999, pp. 25-32.
Hitzenberger, G. et al.: "Pharmacological properties of piracetam." CNS Drugs, vol. 9, No. 1, 1998, pp. 19-27.
P. Enderby: "Effects of Piracetam on Recovery and Rehabilitation after Stroke: A Double-Blind, Placebo-Controlled Study", Clinical Neuropharmacology. vol. 17, No. 4, pp. 320-331, 1994 Raven Press, Ltd.

* cited by examiner

*Primary Examiner*—Ardin Marschel
*Assistant Examiner*—Gregg Polansky
(74) *Attorney, Agent, or Firm*—Sughrue Mion, PLLC

(57) ABSTRACT

The present invention relates to a method for treating a patient having suffered from severe aphasia associated with cerebrovascular accident chronic stage for at least three years, wherein said treatment consists essentially of administering a composition comprising 2-oxo-1-pyrrolidineacetamide as an active ingredient and a pharmaceutically acceptable carrier.

2 Claims, 4 Drawing Sheets

AGENT OR METHOD FOR TREATING SEVERE APHASIA IN CEREBROVASCULAR ACCIDENT CHRONIC STAGE

TECHNICAL FIELD

The present invention relates to an agent or method for treating severe aphasia in cerebrovascular accident chronic stage, which comprises 2-oxo-1-pyrrolidineacetamide (general name: piracetam) as an active ingredient.

BACKGROUND OF THE INVENTION

Aphasia is an disorder in acquired speech functions, which occurs as a result of brain damage (Non-patent reference 1). That is, it means a state in which speech functions (spoken language and written language) once acquired with growth are damaged by a brain injury due to a focus formed by a certain cause in a certain region (language area) of the cerebral hemisphere. Diseases as the cause for aphasia include brain tumor, head injury, cerebrovascular accident and the like. When the brain injury by these diseases is slight and transient, aphasia is also slight. The focus which is large or spread on the center of language area causes severe aphasia and the aphasia is more severe and recovery is difficult as the focus broadens (Non-patent reference 2).

In general, recovery of aphasia is remarkable until 3 months after the onset, gradual improvement continues thereafter, and improvement reaches plateau and symptoms are fixed 1 year after the onset (Non-patent reference 2). However, recovery of functional language is not expected in the case of severe aphasia such as total aphasia (Non-patent reference 3).

Speech therapy (language rehabilitation), which is the sole therapy for aphasia, is carried out by several kinds of methods in accordance with the symptoms of aphasia patients. As the medicinal therapy, sedatives (Sodium amytal, Meprobamate), a vasodilator (PRISCOL®) and the like have been tried from relatively old times, which are not used currently because of no reproducibility of their therapeutic effects.

In addition, a hyperbaric oxygen therapy was tried recently but no effect was found (Non-patent reference 3). From these point, there is no therapeutic method as a pharmacotherapy in Japan now, and there is no drug approved as an aphasia-treating drug.

Even in the case of the language rehabilitation as the only one method for treating aphasia, its application has limitations, and patients having critical aphasia, particularly total aphasia, and patients who already received a systematic language rehabilitation for a certain period of time and the effect reached plateau, are excluded from the subject of treatment (Non-patent reference 3). Since the situation is that no appropriate therapeutic method is available for the patients excluded from the subject of treatment, treatment and care of this disease are taken as a great social problem. Under such a situation, various agents have been investigated with the aim of finding an agent effective for this disease, but an agent which can be judged clinically useful has not been found.

On the other hand, it is known that the compound of formula (I), which is called piracetam as the generic name (trade name: MYOCALM®), shows its effectiveness against the diseases such as motion sickness, excessive movement, increase of tonus, epilepsy and the like (Patent references 1 and 2). In addition, piracetam has the following indications in Europe.

In adults:
  Symptomatic treatment of the psycho-organic syndrome whose features, improved by treatment, are memory loss, attention disorders and lack of drive.
  Treatment of cortical myoclonus, alone or combination.
  Treatment of vertigo and associated disorders of balance, with the exception of dizziness of vasomotor or psychic origin.
  For prophylaxis and remission of sickle cell vaso-occlusive crises.

In children:
  Treatment of dyslexia, in combination with appropriate measures such as speech therapy.
  For prophylaxis and remission of sickle cell vaso-occlusive crises.

However, these diseases do not have any relationship with the disorders of the aforementioned aphasia. In addition, in Europe and U.S.A., therapeutic effect of piracetam is found by the combination use of speech therapy at the acute phase for the aphasia after cerebrovascular accidents. In the non-patent reference 4, investigations were carried out on the improvement of speech disorder in acute ischemia patients, in which 12 g of piracetam was intravenously administered to the patients within 12 hours and then it was administered orally at a dose of 12 g/day for 4 weeks and further at a dose of 4.8 g/day for 8 weeks. However, nothing is known about the clinical therapeutic effect of the present invention for severe aphasia in cerebrovascular accident chronic stage, which passed 3 years or more after onset of the aphasia and has no possibility of being recovered by various treatments.

Non-patent reference 1: *Rinsho Shitsugosho gaku* (Clinical Aphasia), *Igaku Shoin,* 2001, p. 2

Non-patent reference 2: *Rinsho Shitsugosho gaku Handobukku* (Clinical Aphasia Handbook), *Igaku Shoin,* 2000, p. 78, p. 74

Non-patent reference 3: *Shitsugosho no Gengo Chiryo* (Speech therapy of Aphasia), *Igaku Shoin,* 2000, p. 18, p. 48, p. 80

Non-patent reference 4: *CNS Drugs,* 1998, 9, Supple. 1, 41-49

Patent reference 1: JP-B-42-19093

Patent reference 2: U.S. Pat. No. 3,459,738

DISCLOSURE OF THE INVENTION

Problems that the Invention is to Solve

Accordingly, the present invention is to provide an agent or method for treating severe aphasia as a sequela of cerebrovascular accidents.

Means For Solving The Problems

With the aim of finding an agent which shows sufficient efficacy for severe aphasia in cerebrovascular accident chronic stage, the present inventors have conducted extensive studies and, as a result, found that a compound (I) which was completely unconsidered before can exert excellent therapeutic effects on the severe aphasia in cerebrovascular accident chronic stage, thus accomplishing the present invention.

That is, the present invention relates to an agent for treating severe aphasia in cerebrovascular accident chronic stage, which comprises 2-oxo-1-pyrrolidineacetamide (generic name: piracetam) as an active ingredient.

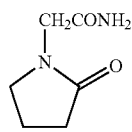

It further relates to a method for treating severe aphasia in cerebrovascular accident chronic stage, which comprises administering an effective amount of an agent comprising piracetam as an active ingredient to a patient having severe aphasia in cerebrovascular accident chronic stage.

It also relates to method for treating severe aphasia, which comprises administering an agent comprising 2-oxo-1-pyrrolidineacetamide as an active ingredient at a dose of from 9 to 40 g/day for a long term of 2 months or more to a patient diagnosed as severe aphasia in cerebrovascular accident chronic stage and having no expectation of improvement in the symptoms even after a passage of 3 years or more of language rehabilitation period.

Advantage of the Invention

Speech therapy was the only one therapy for aphasia of cerebrovascular accident chronic stage before the present invention, and the anguish and exasperation of the patient himself or herself, or the family who care the same, and the speech therapist, were beyond description. Even the presence of such an epoch-making compound was unbelievable in the world. Piracetam brings a hope to the patient and his or her family by dramatically improving this situation, and is safe and has no side effect. Accordingly, the compound represented by formula (I) is excellent as an agent for treating severe aphasia in cerebrovascular accident chronic stage.

BEST MODE FOR CARRYING OUT THE INVENTION

Figure 1:
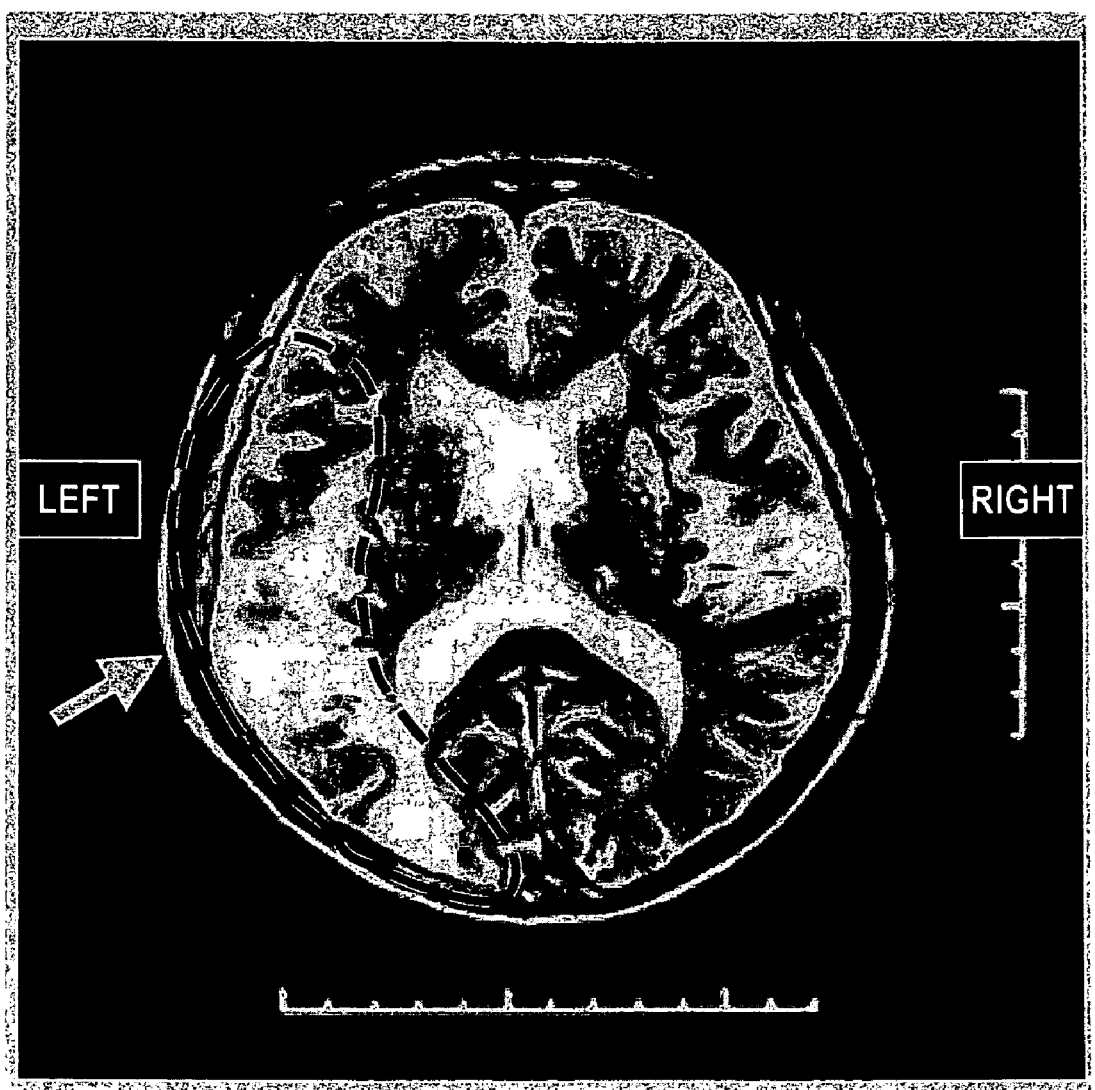
FIG. 1 is a tomogram of temporal plane of the patient of Example 1 measured by a magnetic resonance imaging (MRI) under wakefulness after resting prior to the commencement of the treatment.

The following describes the present invention in detail.

The compound of formula (I) may be prepared, for example, by the method described in JP-B-42-19093 (U.S. Pat. No. 3,459,738). Also, MYOCALM® Solution which comprises the compound of formula (I) as an active ingredient is on sale from Taiho Pharmaceutical Co., Ltd. and the like.

Particularly, regarding a patient diagnosed as a severe aphasia and improvement of the symptoms cannot be expected even after a passage of 3 years or more of language rehabilitation period, more preferable therapeutic effect on aphasia is expected by 2 months or more of long-term administration of administration of the compound represented by formula (I) at a dose of from 9 to 40 g/day. Regarding the dose, administration at from 9 to 24 g/day is preferable, and administration at from 12 to 18 g/day is more preferable. Regarding the administration period, administration for 3 months or more is preferable, and administration for 6 months or more is more preferable. It is desirable to carry out the administration continuously, but several days may be cancelled depending on the symptoms and the state of health of each patient, within such a range that the effect is not reduced. Also, the dose may be optionally increased or decreased depending on the symptoms and the state of health of each patient, within the aforementioned range of dose.

In addition, with respect to a patient having a renal creatinine clearance value of from 20 to 40 ml/minute, among nephropathy patients or patients with reduced renal function, for example, it is also possible to start the administration at an initial dose of about 3 g/day and gradually increase the dose thereafter to the dose of the present invention while checking conditions of the patient.

The "cerebrovascular accident" according to the present invention indicates a general term of the morbid states which bring nervous symptoms by an organic or functional abnormality of the brain blood vessels (*Naika Shindan Kensa Akusesu* (Internal Medicine Diagnosis Inspection Access), *Nippon Iji Shinpo-sha*, 1989). The cerebrovascular accidents are roughly divided into cerebral infarction, cerebral bleeding, subarachnoid hemorrhage and transient cerebral ischemic attack (TIA). The cerebral infarction is a necrosis (softening) of brain tissues by ischemia, and it includes cerebral thrombosis caused by atherosclerosis and cerebral embolism caused by emboli from the extracranial region. The bleeding includes cerebral bleeding into cerebral parenchymal area and subarachnoid hemorrhage into subarachnoid space. A case in which nervous symptoms disappear within 24 hours after onset of the disease is called "transient cerebral ischemic attack", and all of the morbid states are included in the present invention. In addition, the "cerebrovascular accident chronic stage" means a period during which blood pressure and the like general conditions became stable through the improvement of disturbance of consciousness and the like nervous symptoms, after onset of the aforementioned cerebrovascular accidents. Cerebrovascular accident chronic stage may be diagnosed, for example, by neurological examinations by inquiry and the like and by blood pressure measurement and the like scientific inspections.

According to the present invention, the severe aphasia means a case of disease which is regarded as a serious illness based on the severity classification of Goodglass et al. (The assessment of aphasia and related disorders, 2nd ed., Philadelphia, Lea & Febiger, 1983). Also, when applied to the classical classification basic 8 types of aphasia (*Gengosho Gengo Chiryo-no Kiso* (The Basis of Aphasia speech therapy), *Shindan-to Chiryo-sha*, 2003, pp. 37-52), it corresponds to the cases of total aphasia or serious ones among the cases classified into Broca aphasia or Wernicke aphasia. Diagnosis of the severe aphasia may be carried out, for example, by the standard aphasia examination, the CADL examination (practical communication ability test), the WAB aphasia examination, a simple test for aphasia screening (bedside aphasia examination, Motomura, 1992) and the like.

Administration method of the compound represented by formula (I) may be either oral or parenteral administration.

As the administration dosage forms of the compound represented by formula (I), tablets, capsules, powders, granules, injections and the like may be exemplified. These dosage forms can be produced by conventionally known preparation techniques, together with general fillers, disintegrating agents, stabilizers, lubricants, binders and the like additive agents. When solid preparations for oral use are prepared, a binder, a disintegrating agent, a lubricant, a coloring agent, a corrective, a corrigent and the like are added to the active ingredient as occasion demands, and then tablets, coated tablets, granules, powders, capsules and the like can be produced in the usual way. When oral liquid preparations are prepared, solutions for internal use, syrups and the like can be produced in the usual way by adding a corrective, a buffer agent, a stabilizer, a corrigent and the like to the active ingredient. When injections are prepared, injections for subcutaneous, intramuscular and intravenous use can be produced in the usual way by adding a pH adjusting agent, a buffer agent, a stabilizer, a tonicity agent, a local anesthetic and the like to the active ingredient. When rectal suppositories are prepared, suppositories can be produced in the usual way after adding a filler, and a surfactant and the like as occasion demands, to the active ingredient. When ointments are prepared, for example, in the shape of pastes, creams or gels, a generally used base, a stabilizer, a moistening agent, a preservative and the like are formulated in response to the necessity, and mixed and made into the preparations in the usual way. As the base, for example, white petrolatum, paraffin, glycerol, a cellulose derivative, polyethylene glycol, silicone, bentonite and the like can be used. As the preservative, methyl parahydroxybenzoate, ethyl parahydroxybenzoate, propyl parahydroxybenzoate and the like can be used. When adhesive preparations are produced, the aforementioned ointments, creams, gels, pastes or the like may be applied to a general base material. As the base material, woven fabric or nonwoven fabric consisting of cotton, rayon staple or chemical fiber and films, foam sheets and the like of soft vinyl chloride, polyethylene, polyurethane and the like are suitable.

Dose of the compound represented by formula (I) may be optionally increased or decreased in accordance with the symptoms, age and body weight of each patient and degree of the symptoms. In the case of oral administration, the dose is within the range of generally from 9 to 40 g per day per adult, preferably from 9 to 24 g/day, and more preferably within the range of from 12 to 18 g/day, and this is administered once a day or by dividing into several portions.

In addition, in the case of parenteral administration, the dose is within the range of from 9 to 40 g per day per adult, preferably from 9 to 24 g/day, and more preferably within the range of from 12 to 18 g/day, and it is appropriate to administer this by intravenous injection or intravenous infusion injection.

It is possible to make the aphasia-treating agent of the present invention into pharmaceutical preparations by a generally known method and, as the examples, formulation examples using the compound used in the tests of the present invention are shown in the following.

By the use of the aphasia-treating agent of the present invention in combination with other agents, additive effects or synergistic effects can be expected for the prevention and treatment of various diseases. As such agents, cerebral circulation metabolism improving agents (e.g., ibudilast (trade name: Ketas), ifenprodil tartarate (trade name: Cerocral), nicergoline (trade name: Sermion)) and the like may be cited.

Acute toxicity of the compound represented by formula (I) was examined and it has been confirmed that this is a compound having high safety. In addition, according to a therapeutic report from a foreign country, there was no problem on its safety when administered at 60 g/day for gait disturbance of cerebellar degeneration (cf., *Movement Disorder,* 2003, 18, pp. 457-459).

FORMULATION EXAMPLES

Formulation examples of pharmaceutical preparations are described in the following.

Preparation Example 1 Tablet

| | |
|---|---|
| Piracetam | 1200 mg |
| Corn starch | 50 mg |
| Microcrystalline cellulose | 50 mg |
| Hydroxypropylcellulose | 15 mg |
| Lactose | 47 mg |
| Talc | 2 mg |
| Magnesium stearate | 2 mg |
| Ethyl cellulose | 30 mg |
| Unsaturated glyceride | 2 mg |
| Titanium dioxide | 2 mg |

Based on the aforementioned formulation ratio, tablets (1400 mg per tablet) were prepared in accordance with a conventional method.

Preparation Example 2 Granules

| | |
|---|---|
| Piracetam | 1600 mg |
| Lactose | 540 mg |
| Corn starch | 100 mg |
| Hydroxypropylcellulose | 50 mg |
| Talc | 10 mg |

Based on the aforementioned formulation ratio, granules (2300 mg per package) were prepared in accordance with a conventional method.

Preparation Example 3 Capsules

| | |
|---|---|
| Piracetam | 400 mg |
| Lactose | 30 mg |
| Corn starch | 50 mg |
| Microcrystalline cellulose | 10 mg |
| Magnesium stearate | 3 mg |

Based on the aforementioned formulation ratio, capsules (493 mg per capsule) were prepared in accordance with a conventional method.

Preparation Example 4 Injections

| | |
|---|---|
| Piracetam | 3000 mg |
| Sodium chloride | 3.5 mg |
| Distilled water for injection | proper amount |
| | (15 ml per ampoule) |

Based on the aforementioned formulation ratio, injections were prepared in accordance with a conventional method.

Preparation Example 5 Oral Liquid

| | |
|---|---|
| Piracetam | 1200 mg |
| Ethyl parahydroxybenzoate | 5 mg |
| Butyl parahydroxybenzoate | 5 mg |
| Flavor | proper amount |
| Coloring agent | proper amount |
| Purified water | proper amount |

Based on the aforementioned formulation ratio, syrups were prepared in accordance with a conventional method.

EXAMPLES

The present invention is described further in detail in the following using examples, though the invention is not limited thereto.

Test Example 1

Therapeutic Effect for Aphasia in Cerebrovascular Accident Chronic Stage

Among patients of cerebrovascular accident chronic stage (3 years or more elapsed since onset of the illness, and speech therapy is not currently carried out), four patients who have almost no paralysis and can perform eating, excretion and the like daily life, and whose main symptom is aphasia and motor aphasia is its foreground, were subjects in this test. Most of the cases have a past history of the oral administration of anticonvulsants and cerebral circulation metabolism-improving agents, but they were not effective regarding aphasia because of completely no improvement of the symptom. After obtaining consent from the patients or their families, administration of MYOCALM® Solution was started at a dose of from 27 to 36 ml (from 9 to 12 g as piracetam)/day, which was gradually increased or decreased to establish a maintenance dose of 45 ml (15 g as piracetam)/day after about 2 to 4 weeks, and then the administration was further carried out for 4 weeks or more (however, when renal function of the patients was lowered, the administration was carried out by adjusting the initial dose of piracetam to ¼ when the renal creatinine clearance value was from 20 to 40 ml/minute, or the initial dose of piracetam to ½ when the value was from 40 to 60 ml/minute).

Clinical symptoms of aphasia were evaluated based on the following 5 steps, by talking with the patients and learning from their families on the degree of aphasia, using every 4 weeks after the determination of optimum dose as the observing days (cf., the severity classification of Goodglass et al., *Rinsho Shitsugo-sho Gaku Handobukku* (Clinical Aphasia Handbook), *Igaku Shoin*, 2000, p. 82).

1. No spontaneous speech
2. Became able to say a word though not clear in meaning
3. There are words which are babble but can catch somehow
4. Became able to speak though slow
5. Daily communication became not so inconvenient Also, the general improved degree was evaluated based on the following 6 steps of improved degree of aphasia after 12 weeks in comparison with the day of commencement of the administration.

1. Considerable improvement (improvement of 3 steps or more)
2. Moderate improvement (improvement of 2 steps or more)
3. Slight improvement (improvement of 1 step or more)
4. Unchanged
5. Worsened
6. Judgment impossible In addition, development of side effects was examined by carrying out a biochemical blood inspection and a hearing investigation before and after commencement of the administration.

TABLE 1

Therapeutic effects of MYOCALM ® on aphasia of cerebrovascular accident stage chronic

| Example | Sex | Age | Period from onset of illness to start of admin. | Severity classification of Goodglass et al. Before administration | Severity classification of Goodglass et al. After administration | General improvement degree |
|---|---|---|---|---|---|---|
| 1 | male | 83 | 3 years 4 months | 1 | 4 | considerable improvement |
| 2 | female | 68 | 7 years 9 months | 1 | 3 | moderate improvement |
| 3 | male | 69 | 4 years 7 months | 1 | 3 | moderate improvement |
| 4 | male | 59 | 9 years 8 months | 1 | 2 | slight improvement |

As is evident from the above table, the following therapeutic effects were found.

(1) Among 4 cases in total of the examples, high therapeutic effect of 75% as moderate improvement and 100% as slight improvement was found.
(2) There was no problem regarding safety in the all cases also from the clinical test results.

Example 1

A male of 83 years old. Onset of the illness about 4 years ago from speech disorder. Eyes are open, obvious paralysis was not present and order-obeying motion was observed, but the articulation alone was confused and not understandable. An irregular high signal area was found in the left Broca region by MRI (magnetic resonance imaging) and there was arrhythmia, and conservatively treated as cerebral embolism. Left the hospital with remaining the speech disorder only. He was under a course of observation at another hospital, but entered the hospital about 2 years later, because worsening of speech disorder and disturbance of memory turned up and recurrence of new cerebral infarction was found in the left posterior temporal lobe. At that time, obvious paralysis was not present and order-obeying motion was observed, but the conversation was confused to such a degree that its meaning could be barely imagined. ADL (activities of daily living) were independent, but there was no articulation, merely nodding against questions.

From the images of MRI before commencement of the administration of MYOCALM®, broad cerebral infarction was found in the left front lobe, temporal lobe and occipital lobe (FIG. 1).

Administration of MYOCALM® Solution (sales agency: Taiho Pharmaceutical Co., Ltd.) was started about 3 years and 4 months after onset. Since the renal creatinine clearance (Ccr) was 30 ml/minute, the administration was started at a dose of 9 ml (3 g as piracetam)/day, and 2 weeks thereafter, it was able to hear articulation of "I am pretty well". About 3 months after the administration, it was able to tell "I am completely free from inconvenience regarding daily conversation" by himself. One year after the initial administration, the dose was increased to 30 ml (10 g as piracetam)/day and used as the maintenance dose, and by the aphasia examination on the 4th month of the administration, CADL examination (practical communication ability test) showed a value of 4 and the aphasia index (AQ) by the WAB aphasia examination was 62.7, thus showing considerable improvement.

Example 2

A female of 68 years old. Onset of the illness about 9 years ago due to serious subarachnoid hemorrhage. Thereafter, changed hospital for the purpose of carrying out rehabilitation, with maintaining aphasia alone. About 5 years thereafter, took medical advice again because motions became dull. Due to CT, there was no progress of hydrocephalia, but cerebral infarction due to cerebrovascular spasm of left front temporal lobe was found. Paralysis absent and ADL was independent, but the articulation was only simple words. Administration of MYOCALM® Solution was started at a dose of 36 ml (12 g as piracetam) about 7 years and 9 months after onset of the illness. On the 4th month after the administration, she started to say a word of greeting. By the aphasia examination carried out after 1 year and 1 month of the administration, CADL examination showed a value of 3 and the AQ by the WAB aphasia examination was 45.1, thus showing considerable improvement.

Example 3

A male of 69 years old. Onset of the illness about 5 years ago due to cerebral embolism (aphasia). Obvious paralysis was not found, but the speech disorder was obvious with only an articulation of "ah, uh". By the MRI, an old cerebral embolism focus of left front temporal lobe was found.

Figure 2:
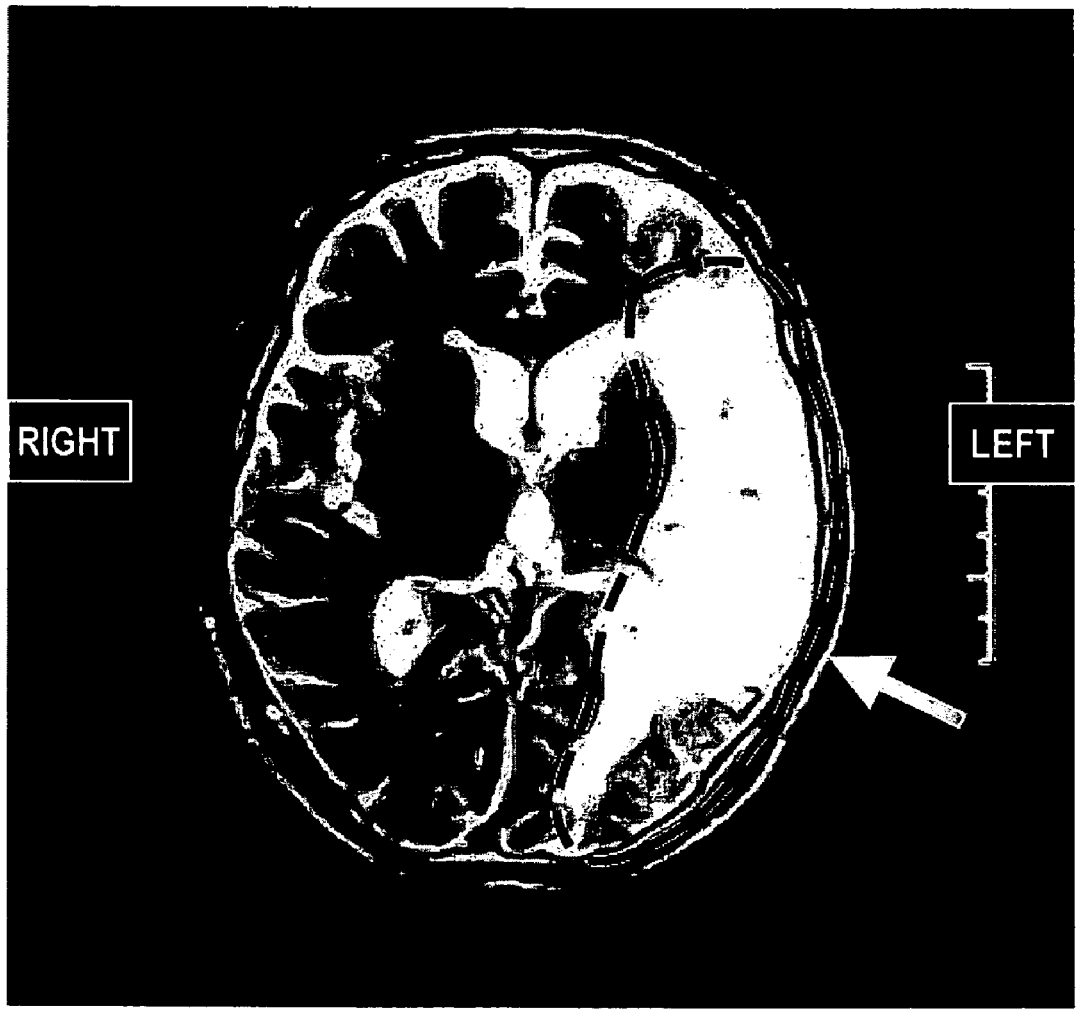
FIG. 2 is a tomogram of temporal plane of the patient of Example 3 measured by MRI under wakefulness after resting prior to the commencement of the treatment.

According to the images of MRI before commencement of the administration of MYOCALM®, they were the states after broad cerebral infarction of the left temporal lobe, frontal lobe and occipital lobe, and in the brain, both of the cortex and gray matter were melted and dropout of nerve cells and nerve fibers was clear (FIG. 2).

Administration of MYOCALM® Solution was started at a dose of 36 ml (12 g as piracetam)/day about 4 years and 7 months after onset of the illness, which was gradually increased to 45 ml (15 g as piracetam)/day and used as the maintenance dose, and the administration was continued for 3 months. After 2 weeks of the administration, the patient was improved to such a level that he can tell his name, and movement of the body was also improved. He became able to say names of people after 1 month, and his speaking vocabulary also became rich after 3 months.

Example 4

A male of 59 years old. Onset of the illness about 10 years ago due to TIA (transient cerebral ischemic attack). Once, ADL became independent by a hospitalization preservative treatment and the patient left the hospital, but cerebral infarction recurred 2 years ago showing speech disorder. At this time, there was no distinct paralysis, there was order-obeying motion and the speech disorder was slight, ADL became independent by a preservative treatment and the patient left the hospital.

Figure 3:
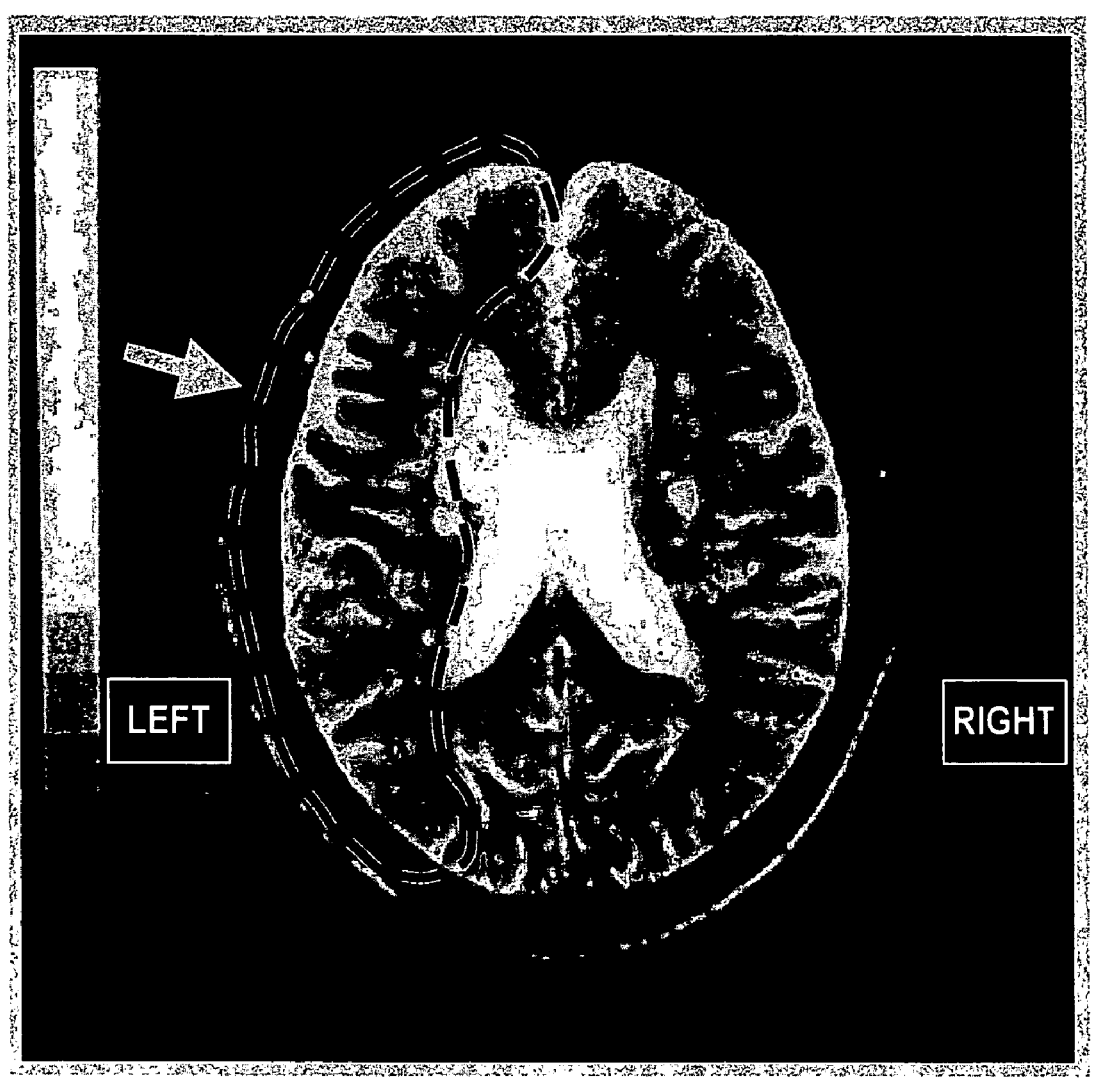
FIG. 3 is a tomogram of temporal plane of the patient of Example 4 measured by MRI under wakefulness after resting at the time of the onset of speech disorder.

The MRA at the time of the onset of the speech disorder showed advanced stricture of left internal carotid artery, and from the images of MRI, multiple cerebral infarction foci and broad and medium degree cerebral atrophy of left frontal, temporal and occipital regions were found (FIG. 3).

Thereafter, the speech disorder became worse, and hardly uttered since 1 year ago.

Figure 4:
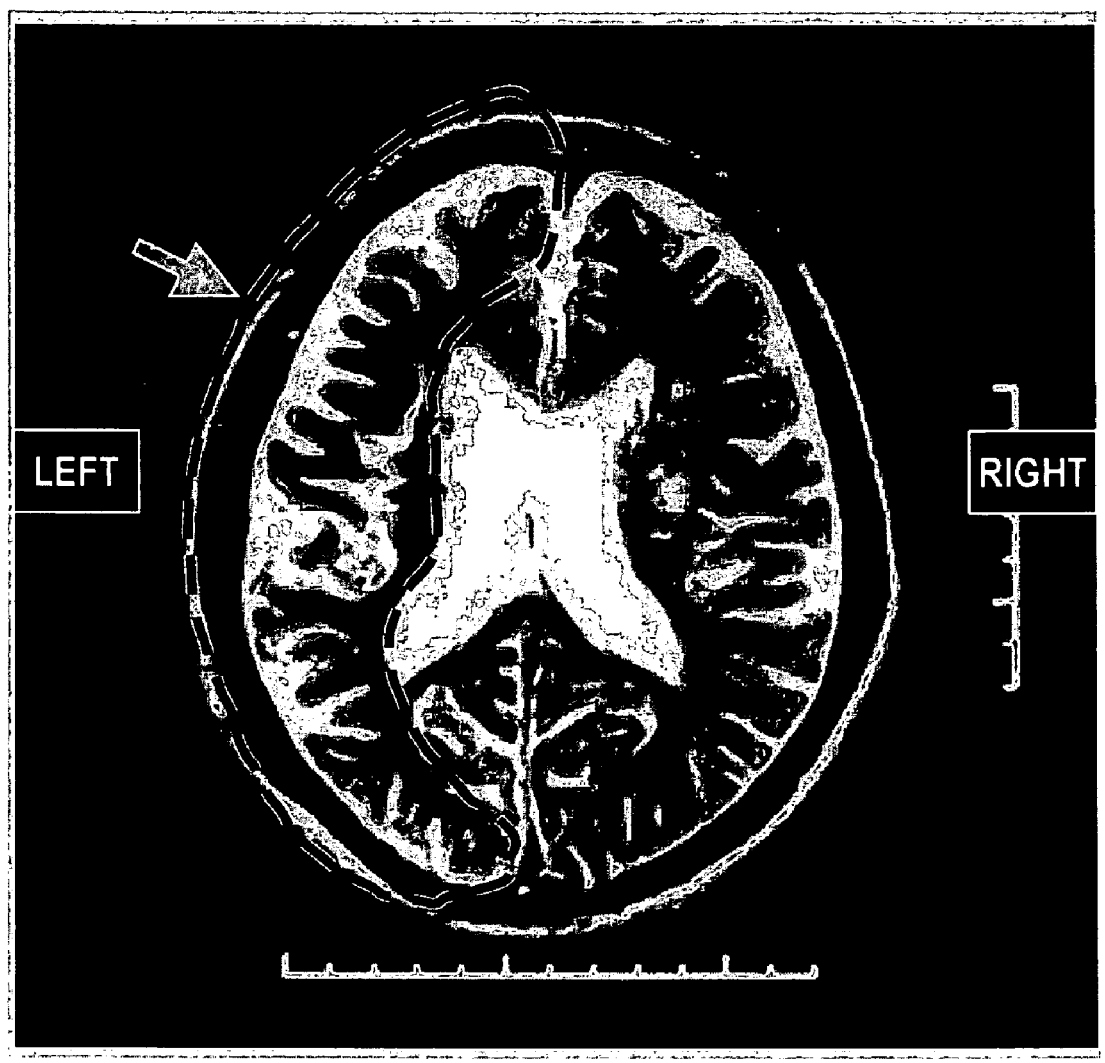
FIG. 4 is a tomogram of temporal plane of the patient of Example 4 measured by MRI under wakefulness after resting prior to the commencement of the treatment.

According to the MRI images before the commencement of MYOCALM® administration, atrophy of left cerebral hemisphere was highly advanced (FIG. 4).

Administration of MYOCALM® Solution was started at a dose of 27 ml (9 g as piracetam)/day about 9 years and 8 months after onset of the illness. This was gradually increased to 45 ml (15 g as piracetam)/day and used as the maintenance dose. At that time thereon, his expression became cheerful, and it became able to perform getting in and out of the car by himself, but the articulation was not yet. On the 3rd month after the administration, he became able to utter confused words, and became able to say simple words such as "ouch!" or "yes" or the like against a question on whether or not the taking of medicine should be continued.

While the invention has been describe in detail and with reference to specific embodiments thereof, it will be apparent to one skilled in the art that various changes and modifications can be made therein without departing from the spirit and scope of the invention.

This application is based on a Japanese patent application filed on Dec. 24, 2003 (Japanese Patent Application No. 2003-427424), the entire contents thereof being thereby incorporated by reference.

INDUSTRIAL APPLICABILITY

The present invention provides a safe and side effect-less agent or method for treating severe aphasia as a secondary disease of cerebrovascular accidents.

The invention claimed is:

1. A method for treating a patient having had severe aphasia associated with cerebrovascular accident chronic stage for at least three years, which consists essentially of administering a therapeutically effective amount of a composition to said patient, wherein said composition comprises 2-oxo-1-pyrrolidineacetamide as an active ingredient and at least one pharmaceutically acceptable carrier, and wherein said patient has had severe aphasia associated with cerebrovascular accident chronic stage for at least three years.

2. A method for treating severe aphasia associated with cerebrovascular accident chronic stage, which comprises administering a composition comprising 2-oxo-1-pyrrolidineacetamide as an active ingredient and at least one pharmaceutically acceptable carrier to a patient diagnosed with severe aphasia associated with cerebrovascular accident chronic stage and with no expectation of improvement in symptoms after at least 3 years of language rehabilitation, and whereby 2-oxo-1-pyrrolidineacetamide is administered to said patient at a dose of from 9 g/day to 40 g/day, for at least 2 months.

* * * * *